US011472620B2

(12) United States Patent
Platt et al.

(10) Patent No.: US 11,472,620 B2
(45) Date of Patent: Oct. 18, 2022

(54) MULTI-CHAMBERED PACKAGE

(71) Applicant: Church & Dwight Co., Inc., Princeton, NJ (US)

(72) Inventors: William D. Platt, Lumberton, NJ (US); Caryn Culleton Oryniak, Hillsborough, NJ (US); Richard James Elliott Gilbert, Belle Mead, NJ (US); Jonathan Andrew Wharton, Ewing, NJ (US); Gerhart P. Huy, Hamilton Square, NJ (US); Michael T. Pinchiaroli, Martinsville, NJ (US); Rajesh Ranjan, Princeton, NJ (US); Velissa Van Scoyoc, Philadelphia, PA (US); Luis C. Muniz, Far Hills, NJ (US); David Schweitzer, Weston, CT (US); Jacob Daniel Taylor, Chicago, IL (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 16/915,083

(22) Filed: Jun. 29, 2020

(65) Prior Publication Data
US 2021/0009331 A1    Jan. 14, 2021

Related U.S. Application Data

(60) Provisional application No. 62/873,476, filed on Jul. 12, 2019.

(51) Int. Cl.
*B65D 75/32* (2006.01)
*B65D 65/38* (2006.01)

(52) U.S. Cl.
CPC .......... *B65D 75/327* (2013.01); *B65D 65/38* (2013.01); *B65D 2221/00* (2013.01)

(58) Field of Classification Search
CPC ... B65D 75/327; B65D 65/38; B65D 2221/00
USPC .......................................................... 206/69
See application file for complete search history.

(56) References Cited

U.S. PATENT DOCUMENTS

| 3,036,705 | A |   | 5/1962  | Haecker           |
|-----------|---|---|---------|-------------------|
| 3,294,230 | A |   | 12/1966 | Penska            |
| D309,258  | S |   | 7/1990  | Vigne             |
| 5,044,492 | A | * | 9/1991  | Auerbach ............... A61F 6/005 |
|           |   |   |         |                   206/69 |
| 5,353,985 | A |   | 10/1994 | Nageli et al.     |

(Continued)

FOREIGN PATENT DOCUMENTS

| BE | 1015797  | 9/2005  |
|----|----------|---------|
| CA | 2258877  | 7/2000  |
| DE | 29811427 | 10/1998 |

*Primary Examiner* — Jacob K Ackun
(74) *Attorney, Agent, or Firm* — Church & Dwight Co., Inc.

(57) ABSTRACT

The present disclosure provides packages that are configured for containing a prophylactic device and a plurality of lubricant compositions. The package can include a primary storage compartment in which the prophylactic device can be contained and a plurality of secondary storage compartments arranged relative to the primary storage compartment, the plurality of secondary storage compartments containing lubricant composition(s). The present disclosure further provides methods for providing a lubricated prophylactic device.

19 Claims, 5 Drawing Sheets

(56) References Cited

U.S. PATENT DOCUMENTS

| | | | |
|---|---|---|---|
| 5,649,624 A | 7/1997 | Seaton | |
| D384,578 S | 10/1997 | Wangu et al. | |
| 5,681,574 A | 10/1997 | Haber et al. | |
| D416,484 S | 11/1999 | Voden | |
| D423,929 S | 5/2000 | Simmers et al. | |
| 6,742,521 B2 * | 6/2004 | McCleskey | A61F 6/005 128/842 |
| D525,879 S | 8/2006 | Ueda et al. | |
| D549,094 S | 8/2007 | Oner et al. | |
| 7,325,703 B2 | 2/2008 | Gherdan et al. | |
| D604,635 S | 11/2009 | Xu | |
| 7,686,160 B2 | 3/2010 | Newman | |
| 7,882,838 B2 | 2/2011 | Mallory | |
| 2005/0045497 A1 * | 3/2005 | Sample | A61F 6/005 206/69 |
| 2005/0109659 A1 | 5/2005 | Hickey et al. | |
| 2008/0118417 A1 | 5/2008 | Mallory | |
| 2008/0173565 A1 | 7/2008 | Staub et al. | |
| 2009/0078606 A1 | 3/2009 | Conley et al. | |
| 2010/0068097 A1 | 3/2010 | Ade et al. | |
| 2010/0206752 A1 | 8/2010 | Nikitczuk et al. | |
| 2012/0048752 A1 * | 3/2012 | Madigan | A61F 6/005 206/69 |
| 2013/0062226 A1 | 3/2013 | Lee | |
| 2014/0174961 A1 * | 6/2014 | Lee | A61F 6/04 206/69 |
| 2017/0181928 A1 | 6/2017 | Collins et al. | |

\* cited by examiner

MULTI-CHAMBERED PACKAGE

CROSS-REFERENCE TO RELATED APPLICATIONS

The present application claims priority to U.S. Provisional Patent Application No. 62/873,476, filed Jul. 12, 2019, the disclosure of which is incorporated herein by reference in its entirety.

FIELD OF THE DISCLOSURE

The present disclosure relates to packages for containing multiple materials. More particularly, the present disclosure relates to a multi-chambered package configured to contain a prophylactic and one or more lubricants.

BACKGROUND

Prophylactics, or condoms, may be provided in a variety of different styles. For example, condoms are sold in both lubricated and non-lubricated forms (i.e., with or without a lubricant composition combined therewith). Lubricated condoms typically are sold with a lubricant pre-applied to one or both of an exterior surface and in interior surface of the condom. The lubricant may be configured for providing extra comfort and/or enhanced stimulation to one or both partners during sexual intercourse. Often, lubricant in excess of the pre-applied amount may be desired by the partners for various purposes, such as foreplay, heightened sensation, massage, or to relieve general vaginal dryness. Commonly, extra lubricant can be purchased separately in multiple use bottles.

Relying upon the provision of added lubricant via a supplementary bottle or other container can be, at a minimum, inconvenient, and can cause embarrassment in the unintended disclosure that an individual is carrying a container of personal lubricant or other material utilized in sexual activity. Sexual activity is often spontaneous, and although it is socially acceptable to ask a sexual partner if they have a condom prior to engaging in sexual activity, it is not as readily acceptable to ask the partner if they have personal lubricant for use in the spontaneous activity. Furthermore, the need and/or desire for personal lubricant may not become evident until after initiation of sexual activity, and accessing a lubricant container or being required to search for lubricant container during sexual activity can be mood-destroying at the time of need. Accordingly, there is a need in the field for means of providing a reservoir of personal lubricant in tandem with a prophylactic such that the personal lubricant is discretely provided, readily available, and easily accessible at the time of need.

SUMMARY OF THE DISCLOSURE

The present disclosure provides packaging that is suitable for storage of and providing ease of access to a prophylactic device (e.g., a condom) and at least one lubricant composition provided in a plurality of compartments. The packaging can include a primary compartment for storage of the prophylactic device and a plurality of secondary compartments for storage of the lubricant composition. The packaging can be adapted to or configured to allow for direct dispensing of the lubricant composition into the primary storage compartment and/or outwardly for external application.

In one or more embodiments, a package according to the present disclosure can comprise: a primary storage compartment containing a prophylactic, the primary storage compartment being accessible through a central opening therein, the central opening being covered with a sealing layer; and a plurality of secondary storage compartments arranged relative to the primary storage compartment, the plurality of secondary storage compartments each containing a lubricant composition. In further embodiments, the package can be defined in relation to one or more of the following statements, which can be combined in any number and order.

The one or more of the plurality of secondary storage compartments can be fluidly communicable with the primary storage compartment.

The one or more of the plurality of secondary storage compartments can be fluidly separated from the primary storage compartment by a frangible seal or a channeled seal.

The sealing layer can be a peel-off layer.

The sealing layer can be removable and re-sealable.

The plurality of secondary storage compartments separately can contain at least two different lubricant compositions.

One or more of the plurality of secondary storage compartments can include a dispensing zone through which the lubricant composition is dispensable by compression of the one or more of the plurality of secondary storage compartments.

The package can comprise a backing layer and a cover layer engaging the backing layer so as to define the primary storage compartment and the plurality of secondary storage compartments.

The primary storage compartment can comprise a bottom boundary formed from the backing layer and a perimeter wall formed from the cover layer, the perimeter wall extending a distance away from the backing layer.

The perimeter wall can terminate in a top flange that defines the central opening in the primary storage compartment.

The sealing layer can engage the top flange.

The cover layer can be compressible and exhibits a self-sustaining rigidity.

The plurality of secondary storage compartments each can comprise a bottom wall formed from the backing layer and a raised wall formed from the cover layer.

The raised wall can comprise a monolithic perimeter wall and top wall formed from the cover layer.

The raised wall can be in the form of a rounded dome.

The raised wall of one or more of the plurality of secondary storage compartments can include a dispensing zone through which the lubricant composition is dispensable by compression of the one or more of the plurality of secondary storage compartments The package further can comprise a plurality of fluid channels individually interconnecting each of the plurality of secondary storage compartments with the primary storage compartment.

The package further can comprise a plurality of frangible seals or channeled seals individually fluidly separating each of the plurality of secondary storage compartments from the primary storage compartment.

The backing layer can comprise a foil lined paper or a polymeric material.

The cover layer can comprise a polymeric material.

In one or more embodiments, the present disclosure can relate to a method of providing a lubricated prophylactic device. For example, such method can comprise: providing a package including a primary storage compartment containing the prophylactic device and including a plurality of secondary storage compartments each containing a lubricant composition; and dispensing the lubricant composition by compressing one or more of the plurality of secondary storage compartments with a force sufficient to cause the lubricant composition contained therein to pass from the compressed secondary storage compartment and one or both of: into the primary storage compartment such that the lubricant composition makes physical contact with the prophylactic device; and away from the primary storage compartment for external dispensing of the lubricant composition. In further embodiments, the method may be defined in relation to one or more of the following statements, which can be combined in any number and order.

The method can comprise compressing at least two separate secondary storage compartments with force sufficient to cause two different lubricant compositions separately contained in the two separate secondary storage compartments to pass from the compressed secondary storage compartments and into the primary storage compartment.

The method can comprise removing a sealing layer from the primary storage compartment so that the prophylactic device is removable therefrom.

The sealing layer can be removed only after dispensing of the personal lubricant composition from at least one of the plurality of secondary storage compartments into the primary storage compartment for combination with the condom.

The method further can comprise at least partially resealing the sealing layer over the primary storage compartment.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to packaging useful for the common provision of a prophylactic device, particularly a condom, and a quantity of at least one personal lubricant composition. The quantity of the at least one personal lubricant composition in particular is commonly packaged but stored separately from the prophylactic device until the time of use. As such, the at least one personal lubricant composition specifically is not provided pre-applied to the prophylactic device.

Packaging for condoms it typically configured to be minimal and discrete. Often, the condom is packaged between sheets of in a heat sealable laminated film of aluminum foil, plastics, and/or paper. As such, the package is typically configured to be torn or cut open for removal of the condom, and the package itself provides little or no use other than storing the unused condom. The presently disclosed packages are adapted to or configured to not only provide protective storage of the condom but also provide options for mixing of lubricant(s) with the condom prior to use and/or for disposing of the condom after use. Moreover, the presently disclosed packages provide unitary storage of the condom as well as the one or more lubricants provided therewith, and the separate storage can be adapted for or configured for allowing for easy dispensing of the one or more lubricant onto the condom.

Figure 1:
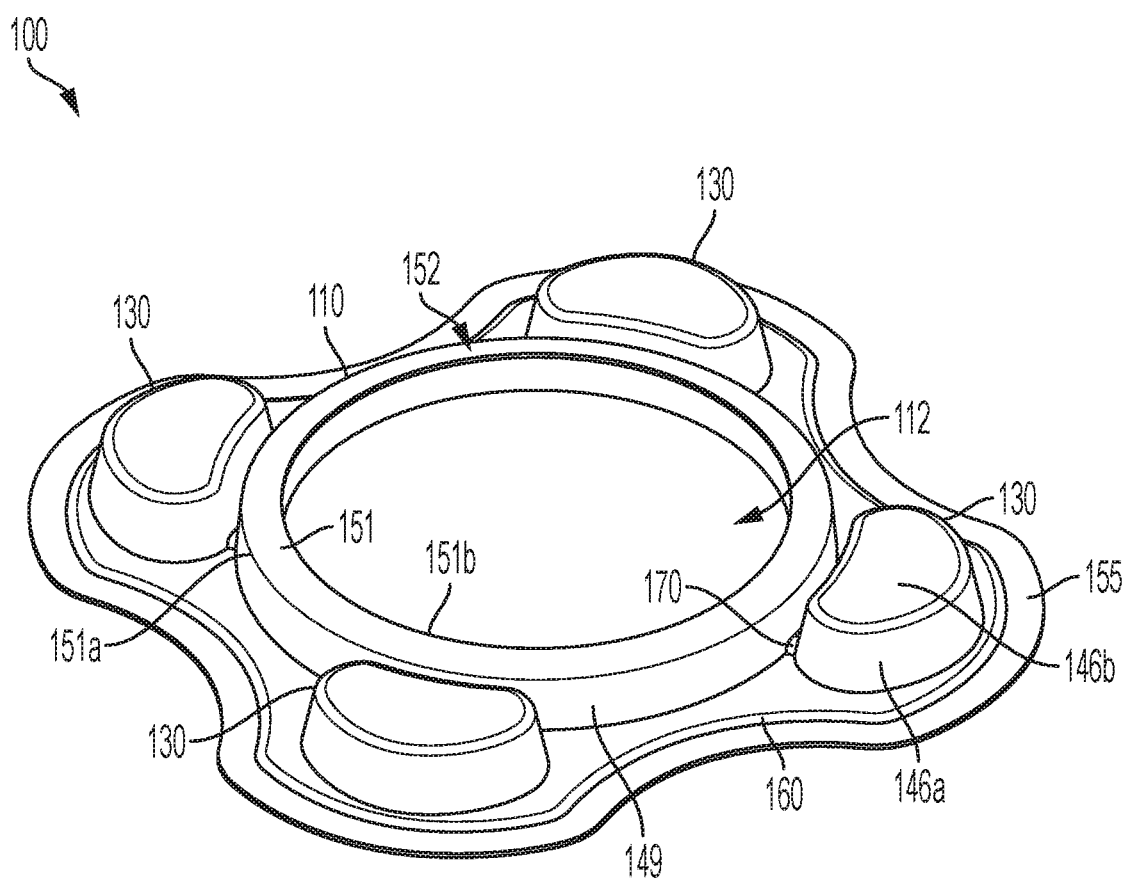
FIG. 1 is a perspective view of a package according to an example embodiment of the present disclosure including a primary storage compartment and four secondary storage compartments.
Figure 2:
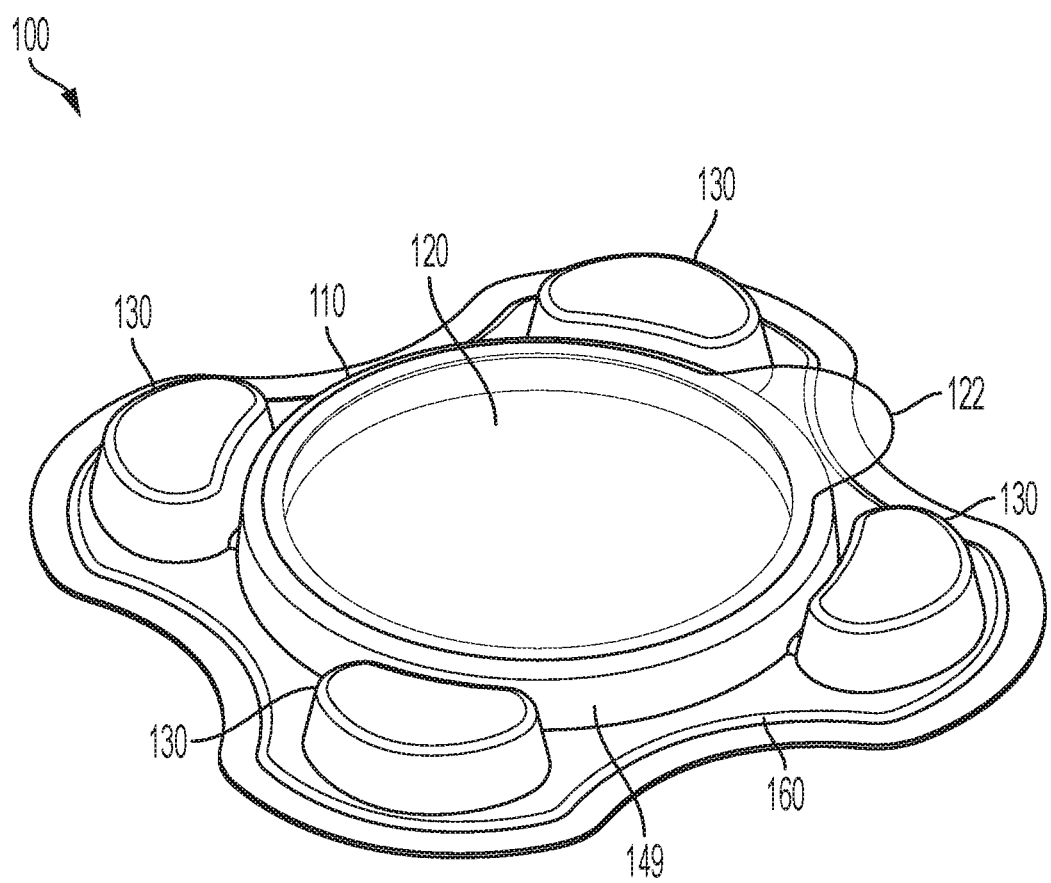
FIG. 2 is a further view of the package of FIG. 1 and further including a sealing layer over the primary storage compartment.

Referring to FIG. 1 and FIG. 2, a package 100 according to embodiments of the present disclosure can comprise a primary storage compartment 110 that is accessible through a central opening 112 therein. The primary storage compartment 110 can be sized and shaped to accommodate a prophylactic, such as a condom, that can be contained therein. A sealing layer 120 can be provided for covering the central opening 112 in the primary storage compartment 110, and the sealing layer can include a tab 122 for use in removing the sealing layer 120 from the package 100. The sealing layer 120, for example, can be a peel-off layer that is adhesively applied to the primary storage compartment 110 and that can be removed therefrom by peeling away from the package 100. The sealing layer 120 can be adapted to or configured to be completely removable from the package 100 without the ability to reapply the sealing layer thereto. In some embodiments, however, the sealing layer 120 can be adapted to or configured to be removable and re-sealable. As such, an adhesive utilized to apply the sealing layer 120 to the primary storage compartment 110 can be reusable adhesive so that the sealing layer 120 can be partially removed from the primary storage compartment and then be re-sealed to the primary storage compartment. The ability to re-seal can reduce the opportunity for lubricant composition that may be present in the primary storage compartment 110 to leak therefrom after removal of the condom and before disposal of the package 100. Further, in some embodiments, the used condom may be replaced into the primary storage compartment 110, and the sealing layer 120 may be re-sealed to the primary storage compartment for a substantially mess-free disposal.

Figure 3:
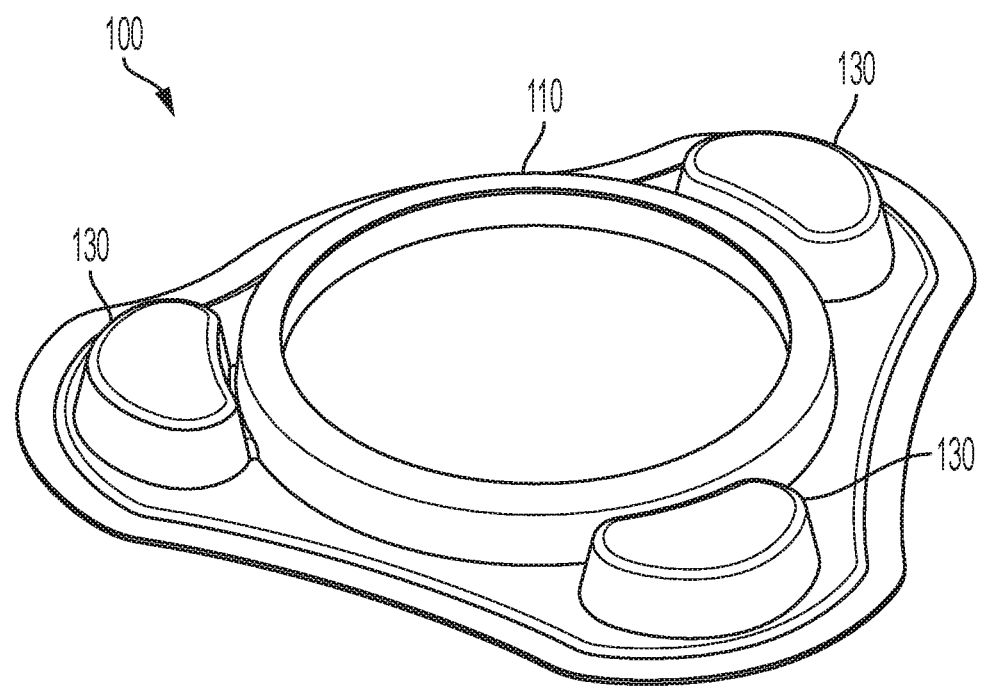
FIG. 3 is a perspective view of a package according to an example embodiment of the present disclosure including a primary storage compartment and three secondary storage compartments.
Figure 4:
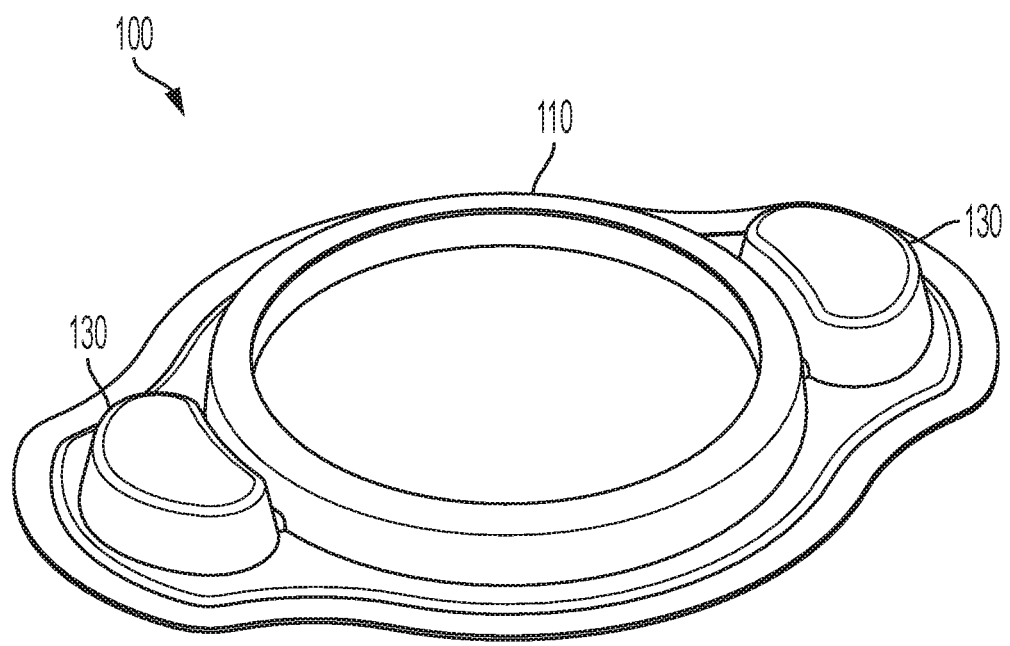
FIG. 4 is a perspective view of a package according to an example embodiment of the present disclosure including a primary storage compartment and two secondary storage compartments.

In addition to the primary storage compartment 110, the package 100 further can include a plurality of secondary storage compartments 130 arranged relative to the primary storage compartment. The plurality of secondary storage compartments 130 each can contain a lubricant composition. Although four secondary storage compartments 130 are illustrated in FIG. 1 and FIG. 2, the present disclosure encompasses any number of secondary storage compartments. For example, in FIG. 3, the package 100 comprises three of the secondary storage compartments 130, and in FIG. 4, the package comprises two of the secondary storage compartments.

Any desired lubricant composition(s) can be provided in the secondary storage compartments 130. In some embodiments, each of the secondary storage compartments 130 can contain the same lubricant composition. In this manner, the maximum quantity of the lubricant composition may be provided in a single package 100. In further embodiments, two different lubricant compositions may be provided. For example, in FIG. 4, a first of the secondary storage compartments may include a first lubricant composition, and a second of the secondary storage compartments may include a second, different lubricant composition. Likewise, in FIG. 3, two of the secondary storage compartments may contain one of the first lubricant composition and the second lubricant composition, and the remaining secondary storage compartment may contain the other of the first lubricant composition and the second lubricant composition. Further, in FIG. 2, two of the secondary storage compartments may contain the first lubricant composition, and two of the secondary storage compartments may contain the second lubricant composition. In other embodiments, three different lubricant compositions may be provided in three different secondary storage compartments. For example, in FIG. 3, a first of the secondary storage compartments may include a first lubricant composition, a second of the secondary storage compartments may include a second, different lubricant composition, and a third of the secondary storage compartments may include a third lubricant composition that is different from each of the first and second lubricant compositions. In still additional embodiments, four different lubricant compositions may be provided in four different storage compartments. For example, in FIG. 1, a first of the secondary storage compartments may include a first lubricant composition, a second of the secondary storage compartments may include a second, different lubricant composition, a third of the secondary storage compartments may include a third lubricant composition that is different from each of the first and second lubricant compositions, and a fourth of the secondary storage compartments may include a fourth lubricant composition that is different from each of the first, second, and third lubricant compositions.

Any personal lubricant composition may be provided in the secondary storage compartments 130. For example, U.S. Patent Publication No. 2018/0153800 to Church & Dwight Co. Inc., the disclosure of which is incorporated herein by reference, discloses lubricant compositions configured for providing sensations, such as warming, cooling, tingling, refreshing, and/or numbing, and any of such compositions can be suitable for use according to the present disclosure. As an example embodiment, one or more of the secondary storage compartments 130 may include a personal lubricant composition that is configured to provide a warming effect, and one or more of the secondary storage compartments may include a personal lubricant composition that is configured to provide a cooling effect. In further embodiments, personal lubricant included in the package 100 may be configured to provide one or more flavors, sensations, and/or aromas. As such, the desired lubricant providing the desired flavor, sensation, and/or aroma may be individually dispensed as desired at the time of use of the condom that is contained in the primary storage compartment 110.

Dispensing of the lubricant composition from the secondary storage compartments 130 can be via a variety of pathways. As further described below, the package 100 can be configured so that the lubricant composition is dispensable through limited means in order to reduce accidental spills of the lubricant and/or to allow for more precise application of the lubricant to the condom stored in the primary storage compartment 110. In some embodiments, one or more of the plurality of secondary storage compartments 130 may be adapted to be or configured to be fluidly communicable with the primary storage compartment 110. For example, as described in greater detail below, one or more of the plurality of secondary storage compartments 130 can be fluidly separated from the primary storage compartment 110 by a sealing member that can be penetrated when desired for dispensing of liquid stored in the plurality of secondary storage compartments. For example, the sealing member can be one or more of a frangible seal, a channeled seal, or the like. In this manner, lubricant composition can be substantially precluded from exiting the package 100 generally as the lubricant composition can be precisely dispensed from the secondary storage compartment 130 directly into the primary storage compartment 110. In some embodiments, one or more of the plurality of secondary storage compartments 130 may include a dispensing zone through which the lubricant composition is dispensable by compression of the one or more of the plurality of secondary storage compartments. The dispensing zone may include the sealing member as noted above. In other embodiments, the dispensing zone may be present on an exterior portion of the secondary storage compartment 130 so that the lubricant composition may be dispensed externally from the package 100. A channeled seal in particular can be useful to maintain a sealing arrangement until the time of desired dispensing of the lubricant composition. The channeled seal can be a sealing arrangement that, when intentionally compromised, will desirably channel the lubricant composition to a desired location. As discussed above, a channeled seal (or other sealing arrangement) can be utilized to channel the lubricant composition toward the primary storage compartment 100. In some embodiments, however, a channeled seal (or other sealing arrangement) can be utilized to channel the contained lubricant composition away from the primary storage compartment and to a dispensing outlet that will allow the lubricant to flow with controlled action to an exterior location (e.g., a finger, a condom, or a sexual organ) where the lubricant can be utilized, for example, to promote foreplay, to provide sexual sensations, for massage, or to provide other eroticism before, during, or after a sexual act.

Figure 5:
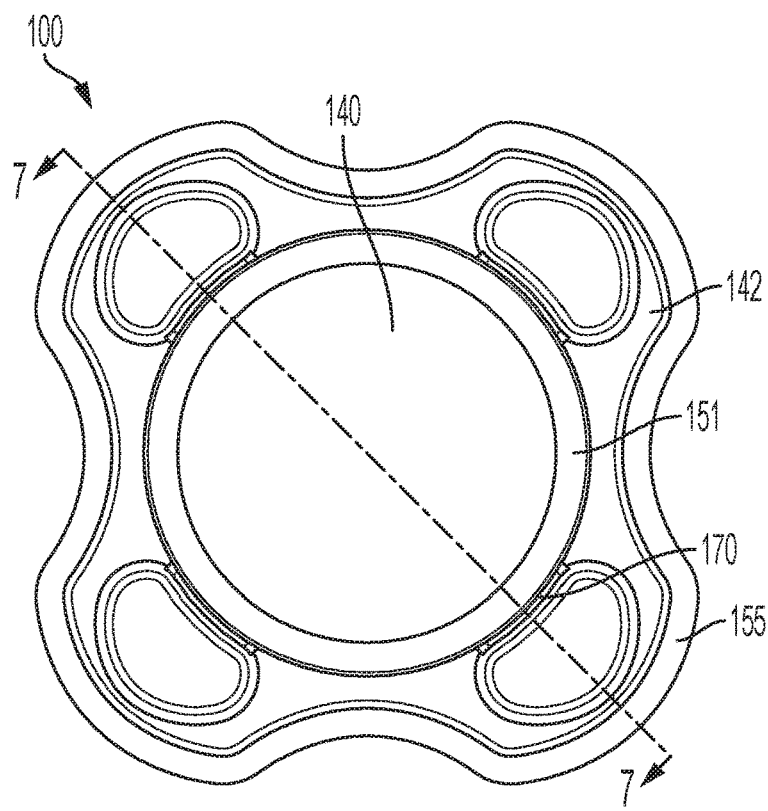
FIG. 5 is a plan view of a package according to an example embodiment of the present disclosure showing a top view thereof.
Figure 6:
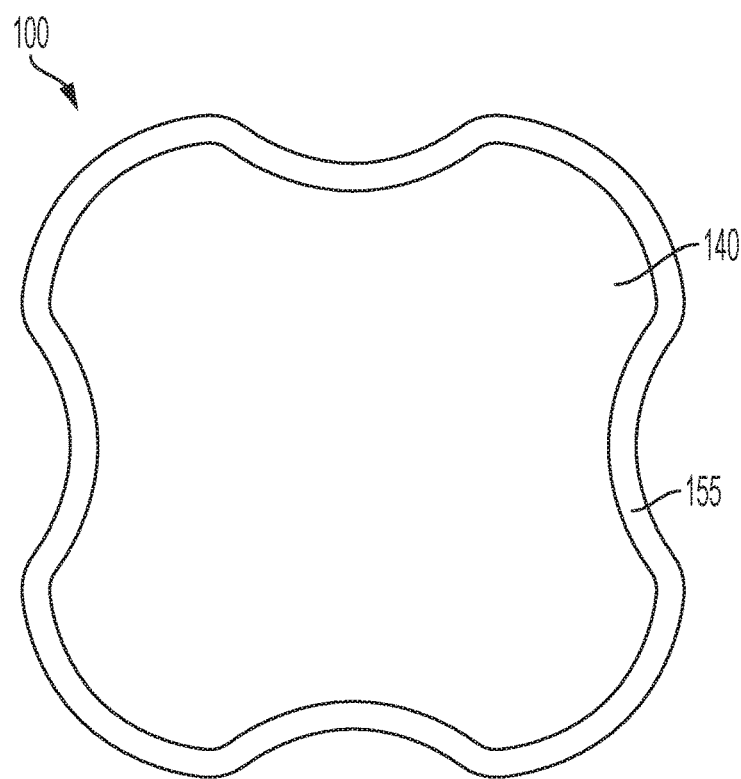
FIG. 6 is a plan view of a package according to an example embodiment of the present disclosure showing a bottom view thereof.
Figure 7:
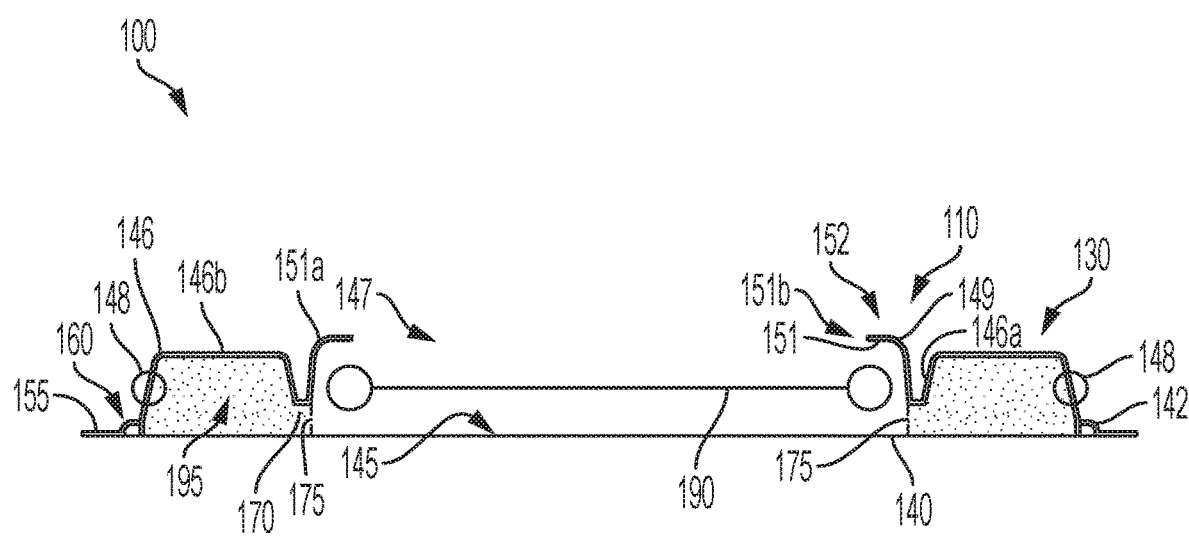
FIG. 7 is a partial cross-sectional view of the package of FIG. 5.

In one or more embodiments, the package 100 may be defined by a plurality of layers that individually may be formed of the same or of different materials. The plurality of layers of materials may be combined to form the primary storage compartment 110 and the secondary storage compartments 130. With reference, for example, to FIG. 5, FIG. 6, and FIG. 7, the package 100 can comprise a backing layer 140 and a cover layer 142 engaging the backing layer so as to define the primary storage compartment 110 and the plurality of secondary storage compartments 130. The backing layer 140 may be at least partially visible through the central opening 112 in the primary storage compartment 110 and thus may form, at least in part, a bottom boundary 145 of the primary storage compartment. In some embodiments, the cover layer 142 may extend at least partially across the bottom boundary 145 of the primary storage compartment 110. As such, the bottom boundary 145 of the primary storage compartment 110 may be formed solely of the backing layer 110, may be formed by both the backing layer and the cover layer 142, or may be formed in part by the backing layer and in part by the cover layer. The bottom boundary 145, in combination with a top boundary 147 that extends across the uppermost portion of the primary storage compartment 110 and a perimeter wall 149 that surrounds the primary storage compartment, can define in interior volume of the primary storage compartment in which a condom or other prophylactic device may be stored or contained. In some embodiments, the top boundary 147 may be at least partially defined by the sealing layer 120. The primary storage compartment 110 thus may be defined by the bottom boundary 145, the perimeter wall 149, and any sealing layer 120 attached to the primary storage compartment.

One or more of the primary storage compartment 110 and the plurality of secondary storage compartments 130 can be sized and shaped to contain a desired prophylactic device (e.g., in the primary storage compartment) and/or a desired content of lubricant composition (e.g., in the secondary storage compartments). For example, in some embodiments, the secondary storage compartments 130 can be sized to contain about 0.25 to about 5 grams, about 0.3 to about 4 grams, or about 0.5 to about 3 grams of liquid lubricant composition. In further embodiments, the secondary storage compartments can be adapted to or configured to contain a predefined amount of liquid lubricant that is predefined based upon one or more of an average amount of lubricant commonly utilized in a single sexual encounter (which average amount may be substantially evenly divided between two or more of the secondary storage compartments), lubricant density, lubricant texture, lubricant viscosity, and lubricant sensational property or properties. In one or more embodiments, the primary storage compartment 110 can be adapted to or configured to contain a condom having an industry standard sizing (e.g., thin, regular, large, or magnum). The primary storage compartment may be sized to contain the condom and include an excess storage volume to accommodate rolling variances (e.g., so that the condom does not get inadvertently pinched during package sealing). Further, primary storage compartment may be sized to contain the condom and include an excess storage volume to accommodate addition of part or all of the lubricant composition that is stored in one or more of the secondary storage compartments. Thus, the primary storage compartment can be adapted to or configured to have a volume sufficient for containing the condom as well as at least substantially all of the lubricant composition stored in one of the secondary storage compartments, at least substantially all of the lubricant composition stored in two of the secondary storage compartments, at least substantially all of the lubricant composition stored in three of the secondary storage compartments, or at least substantially all of the lubricant composition stored in four of the secondary storage compartments.

The perimeter wall 149 of the primary storage compartment 110 can be formed from the cover layer 142. For example, the cover layer 142 can be configured to extend a distance away from the backing layer 140, said distance at least partially defining a height of the primary storage compartment 110. In some embodiments, the perimeter wall 149 can be adapted to or configured to include one or more features at an uppermost portion thereof. Such features can provides strength and/or rigidity to the perimeter wall 149 and/or may provide a top surface 152 to which the sealing layer 120 may be attached. For example, the perimeter wall 149 may terminate at an uppermost portion thereof in a top flange 151. The top flange 151 can extend a distance inwardly from the perimeter wall such that an external edge 151a of the top flange interconnects with the perimeter wall 151, and an internal edge 151b of the top flange defines a perimeter of the central opening 112 of the primary storage compartment 110. As noted above, in some embodiments, the sealing layer 120 can engage the top flange 151, particularly the top surface 152 of the top flange 151.

The backing layer 140 and the cover layer 142 can be formed of a variety of materials. The backing layer 140, for example, can be formed of a paper, such as a foil lined paper, a polymeric material, or other similar material. In some embodiments, the backing layer 140 may be formed of a material particularly suited for receiving words, symbols, colors, or other printing that can impart a nature of the material(s) contained within the package 100. For example, suitable printing can be applied proximate the individual secondary storage compartments 130 to identify the type of personal lubricant stored in a given secondary storage compartment. Likewise, branding, the type of lubricant present on the condom, or other printing may be provided substantially centrally on the backing layer.

The cover layer 142 can be formed of any material exhibiting a self-sustaining rigidity. Such term is understood to indicate that once provided in a final shape, the material is sufficiently rigid to maintain the final shape at least under an applied pressure equal to its own weight. Thus, when the cover layer material is provided in a defined shape, the defined shape will not collapse under its own weight. In some embodiments, however, it also can be preferable for the cover layer material to be compressible. For example, the secondary storage compartments 130 can be compressible to dispensing of the lubricant stored therein. The cover layer 142, in one or more embodiments, can be adapted to or configured to exhibit a strength and/or a compression resistance that is sufficient to withstand the rigor of being handled and carried in clothing pockets, purses, satchels, and/or wallets without being punctured, torn, leaking, or otherwise allowing for release of the liquid lubricant composition. Conversely, the cover layer 142 preferably is sufficiently compressible to allow a male or female user to easily compress the cover layer to actuate dispensing of the liquid lubricant composition without the requirement of excessive force. In one or more embodiments, the cover layer 142 may be adapted to or configured to be sufficiently compressible to provide for dispensing of at least 50% by weight, at least 75% by weight, at least 90% by weight, or at least 95% by weight of the lubricant composition stored in a respective secondary storage compartment through application of compression in the range of about 15 to about 200 pounds of thumb force, about 20 to about 175 pounds of thumb force, or about 25 to about 150 pounds of thumb force.

As such, the cover layer 142 can be defined as being compressible and exhibiting a self-sustaining rigidity. In certain embodiments, the cover layer 142 therefore may be formed from a polymeric material that may be extruded, thermoformed, or otherwise manufactured into a desired shape. The cover layer 142 may be substantially transparent or may be substantially translucent, or may be substantially opaque. Further, the cover layer may be substantially transparent in one or more sections and may be substantially translucent or substantially opaque in one or more sections.

The backing layer 140 may be affixed, adhered, or otherwise attached to the cover layer at one or more points. For example, the backing layer 140 and the cover layer 142 may be glued, heat sealed, welded, or otherwise attached one to another around substantially the complete perimeter of the package 100 along a perimeter seal 155. The backing layer 140 and the cover layer 142 may likewise be attached together in the same or a different manner at one or more further areas of the package 100, such as around part or all of the perimeter of the primary storage compartment 110 (e.g., in the vicinity of the perimeter wall 149), or such as around part of all of a perimeter of one or more of the secondary storage compartments 130.

In some embodiments, it can be beneficial to form the cover layer 142 to provide a sense of depth to the package. Thus, in addition to the primary storage compartment 110 and the secondary storage compartments 130, the cover layer can be shaped to include a package perimeter wall 160 that extends around all or part of the package 100. The package perimeter wall 160 can be adapted to or configured to provide added rigidity and/or strength to the overall package 100 to help in preventing unintended opening, bending, misshaping, or other adverse effects before use of the package contents.

The beneficial aspects of the rigid and compressible nature of the cover layer 142 material can be envisioned particularly in relation to the one or more secondary storage compartments. As illustrated in that appended drawings, the secondary storage compartments 130 can each comprises a bottom wall 145 formed from the backing layer 140 and a raised wall 146 formed from the cover layer 142. The raised wall 146 preferably substantially completely covers the individual secondary storage compartment 130. For example, the raised wall can be defined by a monolithic perimeter wall 146a and top wall 146b formed from the cover layer 142. In some embodiments, the top wall 146b of the secondary storage compartments 130 can be substantially flat; however, a convex or concave shape is also encompassed. For example, the shape of the top wall 146b may be utilized to distinguish between the nature of the personal lubricant that stored in a respective secondary storage compartment 130. In some embodiments, the raised wall 146 may be a single wall that forms substantially a dome shaped compartment.

As the secondary storage compartments 130 are configured for containing a personal lubricant composition, it can be beneficial for the secondary storage compartments to include on or more dispensers through which the lubricant may be accessed. In some embodiments, the raised wall 146 of one or more of the secondary storage compartments 130 can be adapted to or configured to include a dispensing zone 148 through which the lubricant composition is dispensable. As illustrated in FIG. 7, the dispensing zone 148 can be provided on a section of the perimeter wall 146a portion of the raised wall 146 forming the secondary storage compartment 130. For example, the dispensing zone 148 may be a puncturable zone, may include an opening covered by a sealing layer, may be a rupturable zone that is adapted to or configured to break or burst open upon application of pressure, or may be otherwise configured for dispensing of the personal lubricant exterior to the package 100. It is understood that the dispensing zone 148 may be provided additionally or alternatively on the top wall 146b. In one or more embodiments, the personal lubricant may be dispensable from the secondary storage compartment by compression of the secondary storage compartment. Thus, it is beneficial for the cover layer 142 to be formed of a material that provides rigidity as provided above for structural integrity of the overall package 100 while also being compressible (i.e., with the fingers of an adult user) under average adult user conditions. In other words, the cover layer 142 is sufficiently strong such that the secondary storage compartment 130 may substantially resist unintended compression but is sufficiently flexible to submit to a level of compression that is capable of being produced with the fingers of an average adult user.

In some embodiments, the package 100 can include one or more fluid channels 170 individually interconnecting a secondary storage compartment 130 with the primary storage compartment 110. For example, only one secondary storage compartment 130 may be interconnected with the primary storage compartment 110 via a fluid channel 170. Alternatively, a plurality (up to and include all) of the secondary storage compartments 130 may be interconnected with the primary storage compartment 110 via a fluid channel 170. The fluid channel 170 can be adapted to or configured to provide for transfer of the personal lubricant from an individual secondary storage compartment 130 into the volume of the primary storage compartment 170 without requiring external passage. In other words, the personal lubricant composition may be passed directly from the secondary storage compartment 130 into the primary storage compartment 110 through the fluid channel 170. This can be, for example, for the purpose of adding lubricant to the condom stored in the primary storage compartment 110 and/or mixing of different types of lubricant composition that are separately stored in individual secondary storage compartments 130. The fluid channel 170 may be defined by the backing layer 140 and the cover layer 142. The fluid channel 170 further may be integrally formed with one or both of the primary storage compartment 110 and the secondary storage compartment(s) 130. More particularly, the fluid channel 170 may intersect the perimeter wall 149 of the primary storage compartment 110 and/or may intersect the perimeter wall 146a of the secondary storage compartment 130. As illustrated the fluid channel 170 terminates substantially at a perimeter of the primary storage compartment 110. It is understood, however, that the fluid channel 170 may extend a distance into the primary storage compartment 110. For example, the fluid channel 170 may extend into the primary storage compartment a distance that is about 5% to about 45%, about 10% to about 45%, or about 15% to about 45% of the total width of the primary storage compartment. With such distance, the fluid channel 170 can be adapted to or configured to deliver the lubricant composition substantially to a central portion of the primary storage compartment 110 and thus improve delivery to the condom stored therein.

When the fluid channel 170 is present, it can be beneficial to include one or more structural features adapted to or configured to prevent premature dispensing of the personal lubricant from the secondary storage compartment 130 into the primary storage compartment 110. For example, the dispensing zone 148 discussed above may be positioned in a wall that is positioned between the secondary storage compartment 130 and the primary storage compartment. In certain embodiments, the package 100 may be configured to include a frangible seal 175 positioned at one or more of the perimeter wall 146a of the secondary storage compartment 130, the perimeter wall of the primary storage compartment 110, and within the fluid channel 170. The frangible seal 175 can be present in relation to only one of the secondary storage compartments 130 or in a plurality (up to and including all) of the secondary storage compartments present in a given package 100. The frangible seal 175 can be adapted to or configured to fluidly separate a given secondary storage compartment 130 from the primary storage compartment 110; however, the frangible seal can also be adapted to or configured to be breakable, rupturable, or otherwise openable through pressure of the lubricant composition against the frangible seal. For example, when a user compresses a secondary storage compartment 130, the pressure of the liquid within the secondary storage compartment exerting against the frangible seal 175 can cause the frangible seal to break or rupture so that the liquid personal lubricant can be dispensed from the secondary storage compartment into the primary storage compartment 110.

In one or more embodiments, the present disclosure further provides methods of lubricating a condom. In particular, a package 100 as otherwise described herein can be provided with a condom 190 contained in a primary storage compartment 110 and one or more personal lubricant compositions 195 contained in a plurality of secondary storage compartments 130. The method can include compressing one or more of the plurality of secondary storage compartments 130 with force sufficient to cause personal lubricant composition 195 contained therein to pass from the compressed secondary storage compartment and into the primary storage compartment 110 such that the personal lubricant composition makes physical contact with the condom 190. In some embodiments, the method can comprise compressing at least two separate secondary storage compartments 130 with force sufficient to cause two different personal lubricant compositions separately contained in the two separate secondary storage compartments to pass from the compressed secondary storage compartments and into the primary storage compartment 110 such that the personal lubricant compositions makes physical contact with the condom 190. The two separate secondary storage compartments may be compressed simultaneously or sequentially in any order and with sufficient force so that a desired content of the personal lubricant is dispensed into the primary storage compartment. In this manner, the two different personal lubricant compositions may be intermixed within the primary storage compartment to provide for reduced mess and to ensure that the condom is properly lubricated prior to application. In some embodiments, the method further can comprise removing a sealing layer 120 from the primary storage compartment 110 so that the condom 190 may be removed therefrom for application. The sealing layer may be partially removed prior to dispensing the personal lubricant composition(s) into the primary storage compartment 110 as this can be useful to reduce the pressure needed to dispense the personal lubricant composition(s) from the secondary storage compartment(s). Alternatively, the sealing layer may be left in place so that the condom is not removed from the package 100 prior to applying the personal lubricant composition(s) thereto. Thus, the sealing layer may be removed only after dispensing of at least one personal lubricant composition from a secondary storage compartment into the primary storage compartment for combination with the condom.

As previously noted, the sealing layer 120 may be adapted to or configured to be re-sealable. As such, in some embodiments, the methods may comprise re-inserting the condom into the primary storage compartment and at least partially re-sealing the sealing layer over the opening of the primary storage compartment. Alternatively, the method may comprise at least partially re-sealing the sealing layer over the opening of the primary storage compartment without re-inserting the condom. This can be beneficial to prevent leakage of unused personal lubricant from the primary storage compartment prior to discarding of the package.

Where various numerical values are modified herein with use of the word "about" and/or the word "substantially" it is understood that the values can mean the exact value stated. The stated value as modified by the word "about" and/or the word "substantially", however, can vary by a relatively small amount, such as +/−5%, +/−4%, +/−3%, +/−2%, or +/−1% of the exact value.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A package comprising:
    a primary storage compartment containing a prophylactic, the primary storage compartment being accessible through a central opening therein, the central opening being covered with a sealing layer; and
    a plurality of secondary storage compartments arranged relative to the primary storage compartment, the plurality of secondary storage compartments each containing a lubricant composition;
    wherein one or more of the plurality of secondary storage compartments is fluidly communicable with the primary storage compartment.

2. The package of claim 1, wherein one or more of the plurality of secondary storage compartments is fluidly separated from the primary storage compartment by a frangible seal or a channeled seal.

3. The package of claim 1, wherein the sealing layer is a peel-off layer.

4. The package of claim 1, wherein the sealing layer is removable and re-sealable.

5. The package of claim 1, wherein the plurality of secondary storage compartments separately contain at least two different lubricant compositions.

6. The package of claim 1, wherein one or more of the plurality of secondary storage compartments includes a dispensing zone through which the lubricant composition is dispensable by compression of the one or more of the plurality of secondary storage compartments.

7. The package of claim 1, wherein the package comprises a backing layer and a cover layer engaging the backing layer so as to define the primary storage compartment and the plurality of secondary storage compartments.

8. The package of claim 7, wherein the primary storage compartment comprises a bottom boundary formed from the backing layer and a perimeter wall formed from the cover layer, the perimeter wall extending a distance away from the backing layer.

9. The package of claim 8, wherein the perimeter wall terminates in a top flange that defines the central opening in the primary storage compartment.

10. The package of claim 9, wherein the sealing layer engages the top flange.

11. The package of claim 7, wherein the cover layer is compressible and exhibits a self-sustaining rigidity.

12. The package of claim 7, wherein the plurality of secondary storage compartments each comprises a bottom wall formed from the backing layer and a raised wall formed from the cover layer.

13. The package of claim 12, wherein the raised wall comprises a monolithic perimeter wall and top wall formed from the cover layer.

14. The package of claim 13, wherein the raised wall is in the form of a rounded dome.

15. The package of claim 12, wherein the raised wall of one or more of the plurality of secondary storage compartments includes a dispensing zone through which the lubricant composition is dispensable by compression of the one or more of the plurality of secondary storage compartments.

16. The package of claim 7, wherein the package further comprises a plurality of fluid channels individually interconnecting each of the plurality of secondary storage compartments with the primary storage compartment.

17. The package of claim 16, wherein the package further comprises a plurality of frangible seals or channeled seals individually fluidly separating each of the plurality of secondary storage compartments from the primary storage compartment.

18. The package of claim 7, wherein the backing layer comprises a foil lined paper or a polymeric material.

19. The package of claim 7, wherein the cover layer comprises a polymeric material.

\* \* \* \* \*